United States Patent
Borden et al.

(10) Patent No.: US 8,557,237 B2
(45) Date of Patent: Oct. 15, 2013

(54) CRÈME COMPRISING ENCAPSULATED BROMELAIN FOR THE SKIN, SPECIFICALLY FOR INHIBITING INGROWN HAIR

(75) Inventors: Venue C. Borden, New York, NY (US); Carol Artiss, Fountain Valley, CA (US)

(73) Assignee: MindfulnessFYB, Inc., New York, NY (US)

( * ) Notice: Subject to any disclaimer, the term of this patent is extended or adjusted under 35 U.S.C. 154(b) by 922 days.

(21) Appl. No.: 12/353,124

(22) Filed: Jan. 13, 2009

(65) Prior Publication Data

US 2010/0178284 A1      Jul. 15, 2010

(51) Int. Cl.
*A61K 38/43* (2006.01)
*A61K 38/46* (2006.01)
*A61K 33/04* (2006.01)

(52) U.S. Cl.
USPC ........................................ 424/94.65; 424/702

(58) Field of Classification Search
USPC ........................................................ 424/94.65
See application file for complete search history.

(56) References Cited

U.S. PATENT DOCUMENTS

| 4,518,614 | A  | * | 5/1985  | Parkinson    | 514/18.8 |
| 2005/0266064 | A1 | * | 12/2005 | McCarthy     | 424/450  |
| 2006/0142394 | A1 | * | 6/2006  | Kapitz et al. | 514/625  |
| 2006/0246054 | A1 | * | 11/2006 | Chen et al.  | 424/94.65 |

* cited by examiner

*Primary Examiner* — Gyan Chandra
(74) *Attorney, Agent, or Firm* — Andrew S. Langsam; Pryor Cashman LLP

(57) ABSTRACT

A crème for use in connection with the treatment and prevention of ingrown hair. The crème basically comprises a carrier, preferably water and an active amount of encapsulated bromelain, the encapsulated bromelain preferably comprising an inert silicone, preferably cyclomethicone. Other components can be added to the composition, for example, beeswax, sunflower seed oil, shea butter and/or Tea Tree oil. The crème can be used to treat acne, as well.

12 Claims, No Drawings

CRÈME COMPRISING ENCAPSULATED BROMELAIN FOR THE SKIN, SPECIFICALLY FOR INHIBITING INGROWN HAIR

BACKGROUND OF THE INVENTION

The present invention relates to the field of body care and personal hygiene. More specifically, the present invention is a non-comedogenic composition containing nano-encapsulated bromelain (and water and other components) for moisturizing, blending into the skin and skin tones, and for reducing ingrown hair at the sites where hair has been removed for cosmetic reasons. In this connection non-comedogenic refers to the composition being non-skin occlusive, in contrast to comedones which are, for example, acne and blackheads. In its now preferred embodiment, composition and use, the product is intended to be used by a human male or female at or near areas where removal and/or reduction of hair growth is desired and where such removal can result, if untreated, in ingrown hair. Thus, the present invention is used to desirably reduce or eliminate the irritation, rash, discomfort and occurrence of ingrown hair associated with various manners of reducing or eliminated unwanted hair.

DESCRIPTION OF THE PRIOR ART

The prior art contains various attempts to reduce the irritation, rash, discomfort, etc. of ingrown hairs as a consequence of various methods of removing unwanted hair from various areas of the human body. While the present invention is intended for primary use among women who remove unwanted hair from pubic areas, in a bikini wax or Brazilian waxing, the present invention is intended for use anywhere on the human (male and female) body where unwanted hair is removed (for example, many African American men suffer from ingrown hair symptoms when shaving their face) or sought to be reduced and the possibility of ingrown hair is a result therefrom. The composition of the present invention is intended to soothe and ameliorate the irritations of rash from shaving, waxing, hair removal, etc. and to also inhibit and/or reduce the discomfort and occurrence of ingrown hair which often results from hair growth procedures, whether reduction in hair growth and/or hair removal.

The composition of the present invention comprises, inter alia, water and nano-encapsulated bromelain, the latter being the active ingredient/component for the efficacy of the composition for its intended use. Bromelain is an enzyme found in the stems of pineapples. Such an enzyme has been used before for cosmetic compositions but in its natural formulation it is a believed to be relatively unattractive due to its caramel colored. The present inventors have sought, therefore, to utilize the active ingredient of bromelain for a skin soothing and cosmetic application but have sought to whiten the color of the otherwise caramel color of the crème-like composition, to make the product more acceptable and pleasant to apply by consumers. By seeking to make the crème color of the bromelain composition whiter from the original or natural caramel coloration, the bromelain is encapsulated in an inert silicone and cosmetic grade exterior. It has been discovered by the present inventors that the nano-encapsulation of the bromelain not only produces an enhanced coloration to the product, one that is perceived to be more acceptable to the consumer but the nano-encapsulated bromelain product is far more efficacious in its ability to inhibit hair growth, to reduce irritation from hair removal and to inhibit ingrown hair.

Naturally occurring bromelain, the enzyme form the stem of a pineapple, has been used in cosmetic applications for ingrown hair reduction. However, prior to the present invention, there has been no use of nano-encapsulated bromelain for this purpose. Thus, the use of nano-encapsulated bromelain as the active ingredient has been discovered to provide a commercially acceptable color (whiter) for purchase and use by a consumer and, in addition, it has also, surprisingly been found to be very effective at reducing the problems of ingrown hair.

The present invention, a cosmetic product intended to be used by women for soothing and ameliorating irritation or rashes due to shaving or waxing sensitive areas, where ingrown hair can occur, has been found to be far more efficacious than natural bromelain and, in addition, as mentioned, presents as a whiter and thus more visually pleasing cosmetic composition for application. Application initially provides moisture to those affected areas and the non-comedogenic aspect of the product prevents further hair growth (or reduces the thickness of future hair growth) and/or soothes the irritation and rash of ingrown hair as a consequence of shaving and hair removal by waxing or other methods/mechanisms.

Bromelain is a known anti-inflammatory composition. However, when the bromelain is encapsulated, consistent with the current inventors' invention, the new composition both enhances body moisturization and reduces the occurrence of ingrown hair. Encapsulating the bromelain allows the color of the resulting cream-like composition to be a much more visual-pleasing color (in contrast to the coloration of the prior art creams wherein non-encapsulated bromelain was perceived as too pasty, caramel colored and, while capable of visually and discretely blending into many skin tones, presented to the consumer as an unappealing color for consumer's to purchase for such use. The whiter composition is far more commercially appealing and more efficacious.

The present composition satisfies the desire of providing a ingrown hair application composition which is relatively white and effective. My providing nano-encapsulated bromelain as the active ingredient in the composition, a whiter looking application is presented to the consumer which is efficacious for its intended use. Furthermore, while the prior art teaches, as suggested above, the use of naturally occurring bromelain for a crème product, such a crème has been shown and known to turn brown, over time, not as a function of oxidation but, rather, as a consequence of some form of thermal turning. The present invention, by starting off as a whiter composition will tend to stay whiter and seems to have an improved shelf-life, i.e., it will more gradually, if at all over a reasonable time, change colors.

Encapsulation of various homeopathic or man-made medicinal compositions (even other enzymes) have been provided and considered in the past, too. The function of those compositions, however, was to decrease swelling and bruising as a consequence of anticipated surgery. To the inventors' knowledge, however, there has been no teaching nor suggestion in the prior art of nano-encapsulating bromelain, which produces a crème product of superior or whiter color, more commercially acceptable by a consumer, a longer shelf life in terms of maintaining an acceptable coloration for application by the consumer and, in addition, providing an end product which is superior to natural bromelain products for the intended use in connection with the rash and irritation of ingrown hair, a product of the removal or inhibition of unwanted hair growth.

It is believed that the present composition, with an active ingredient of nano-encapsulated bromelain, is also an acne inhibitor and/or the reduction of the irritation and rashes, a soothing of the effects of acne.

Particles of about 20 nano particles or 0.02 microns or less in diameter or size can pass through the surface of the human skin. If in that range, the product may need regulatory approval and/or manufacturing plant approval. The present invention contemplates the use of nano-encapsulated bromelain particles in the range of about 500 to 800 nano particles or 0.5 to 0.8 microns. With this size, the particles can not pass through the pores of the skin and thus the present invention, while perceived as efficacious for its intended purpose, need not be the subject of extensive clinical trials, is not subject to the FDA approval process, nor monitoring by the FDA authorities at the manufacturing site. This allows for a lower cost per unit since the costs of the regulatory scheme need not be amortized into the cost per unit. A less expensive end product is thus presented. Without passing into the body, the present invention is sold as a cosmetic product, which is, in the US, relatively self-regulated, in contrast to a product intended to pass into the body by ingestion or passage therein through the skin.

The nano-encapsulation of the bromelain enzyme also results in a smoother and more even application of the resultant crème product. This is believed to be the reason why the product is seemingly more efficacious that natural (and non-encapsulated) bromelain enzyme. The product serves as a hair growth inhibitor since hair which regrows back in to the original location from which hair has been removed, after application of the crème product, is finer and/or is less thick in terms of numbers of hair per unit area. Over time, it is believed that application of the crème product will result in no hair regrowth to the applied area.

The prior art shows the use of many standard components of a crème composition for making the same more commercially acceptable, from the perspective of, for example, color, smoothness, shelf-life, smell, texture, etc. The present invention uses many of those same components in the end product for substantially the same reasoning. However, as mentioned the present invention is the first to use nano-encapsulated bromelain, in a silicone shell, as the active ingredient with the other components, for a crème/cosmetic product which is whiter than the prior art, is easy to apply, and is more efficacious in treatment of the problems inherent in hair removal, namely, ingrown hairs.

SUMMARY OF THE INVENTION

The present invention is a crème composition whose primary active ingredient is nano-encapsulated bromelain. Of course, the crème composition comprises many other ingredients, most being present for well-known to the prior art reasons, e.g., shelf-life; color; smell, texture, smoothness, ease of application, moisturizing; evaporation, etc. In its preferred composition, the ingrown hair treating crème composition includes water; stearic acid; butylene glycol; caprylic or capric triglycerides; the stated and important, bromelain nanospersion, helianthus annuus (sunflower) seed oil; glycerin and triethanolamine. In addition, as potential included ingredients having 1% or less of the composition by weight, in no particular order and one or more of the following may be selectively included, are the following additional components of the composition:

Dimethicone; cetyl alcohol; polysorbate 80; gylceryl stearate SE; phenoxyethanol; caprylyl glycol; ethylhexyglycerin; hexylene glycol; acrylates/c10-30 alkyl acrylates cross polymers; butyrospermum parkii (shea butter); melaleuca alternifolia (Tea Tree) oil; disodlum EDTA; and Tocopheryl acetate. Beeswax, too, may be an ingredient into the end product, as an emulsifier for the bromelain, as the bromelain is not easily dissolvable in water.

The nanosome complex containing bromelain assists exfoliation and also acts as a topical anti-inflammatory. It is a soother of the skin, the irritation and rashes associated with removal of hair in sensitive areas and facilitates the reduction and elimination of the problems of ingrown hair, consequence of unwanted hair growth and treatment.

The use of a silicone-based nanosphere to encapsulate the bromelain enzyme allows the enzyme to stay active, longer and maintains the enzyme stable, for long-term usage. The crème is quick penetrating and does not leave a heavy film on the surface of the skin. The sunflower seed oil and the shea butter add emolliency and moisturization without fear of skin outbreak. The Tea Tree Oil is believed to keep the skin clear looking.

Because of the small size of the nanospheres of the bromelain enzyme within the crème composition, the skin is less prone to breaking out into a rash or allergic reaction and the spheres of the composition do not plug the holes of the skin. This is believed to be among the mechanisms which allow for the composition to be useful as an ingrown hair reducer/treatment. Irritation and pimples/blackheads are reduced as a consequence of the use of the nano-encapsulated bromelain.

In the preferred embodiment, as now known by the inventors, the nano-encapsulated bromelain particles are a small component by weight of the active ingredient of the composition, with the remainder primarily comprised of water. According to the preferred embodiment, the water and bromelain nanospersion are supplemented with one or more of the following: stearic acid; butylenes glycol; caprylic/capric Triglycerides; helianthus annuus (sunflower) seed oil; glycerin; and triethanolamine. At that level of concentration, the crème composition is believed stable.

Technically, each nanocapsule of bromelain contains a 30% concentration of a 10% solution of the bromelain. In effect, it is a 3% bromelain composition. Then, the ingrown hair crème itself only contains about 5%, by weight, of the 3% composition of bromelain nanospersion. Thus, there is only about 0.15% of the bromelain enzyme in the now-preferred embodiment of the crème. It is currently believed that the nano-encapsulated crème has other potential usages. Ongoing experimentation is believed likely to result in optimizing composition, additives, parameters and usages, etc.

In the preferred embodiment, the carrier or encapsulating material is cyclomethicone, an inert silicone, in this case, preferably of cosmetic grade.

DESCRIPTION OF THE INVENTION AND THE PREFERRED EMBODIMENT

According to the present invention, a new crème product is provided with an active ingredient consisting of nano-encapsulated bromelain. These nano-spherical particles, made preferably from cyclomethicone, an inert silicone, but of cosmetic grade, provides the crème with a whitish color and, in addition, provides a highly efficacious crème for soothing the irritation and rash of ingrown hair, a consequence of hair removal procedures. The crème is easy to apply, blends in well, has a fine shelf life and is smooth. The crème acts as an exfoliant, too. The bulk of the crème is made with water and none, one or more of the following additional components: stearic acid; butylenes glycol; caprylic/capric Triglycerides; helianthus annuus (sunflower) seed oil; glycerin; and triethanolamine. In addition, beeswax may be added to the crème as an emulsifier for the bromelain, since the bromelain is not believed easily miscible with water. According to the present preferred embodiment of the present invention, the size of the nano particles of the encapsulated bromelain are in the range of about 500-800 nano particles or about 0.5 to 0.8 microns. As such it is believed to be too large to pass through the skin of a human, which normally allows particles only 0.02 microns (2 nano particles) or less.

According to the present invention, the nanocapsule of bromelain is made to contain a 30% concentration of a 10% solution of bromelain. So, basically, that is the equivalent of 3% bromelain concentration. The crème contains only about 5% by weight of the 3% bromelain composition with the other listed components making up the balance. Thus, the current best mode or preferred embodiment contains only about 0.15% of the bromelain in the crème.

According to the method of making the novel and inventive composition, the bromelain is encapsulated in a carrier, in the preferred embodiment the exterior of the capsule is an inert silicone, preferably, cyclomethicone. This provides the composition with a smoothness, coverage, and enhances the shelf life and efficacy of the crème, as an inhibitor of hair growth, as a soother of the irritation of rash and discomfort as a consequence of hair removal from sensitive areas, etc. The basic composition, water and encapsulated bromelain is a cosmetic crème which is intended to reduce the problems of ingrown hair.

According to the preferred embodiment of the invention, the other components of the crème composition can include the above listed components. In addition, one or more (or none) of the following components can also be added to the composition, as desired for purposes of adjusting other parameters and features, e.g., smoothness, color, texture, smell, shelf-life, etc.:

Dimethicone; cetyl alcohol; polysorbate 80; gylceryl stearate SE; phenoxyethanol; caprylyl glycol; ethylhexyglycerin; hexylene glycol; acrylates/c10-30 alkyl acrylates cross polymers; butyrospermum parkii (shea butter); melaleuca alternifolia (Tea Tree) oil; disoldium EDTA; and Tocopheryl acetate. These additives are generally added to the water and encapsulated bromelain in amounts, by weight, whereby each additive is present in an amount less than about 1% each.

The subject invention can be made by many commercial cosmetic manufacturers as it is believed that they generally posses the ability to formulate a composition comprised primarily of water and encapsulated bromelain. Dynamic Cosmetic, Inc. of Newtown, Pa., (Phone 215 3231-5496) with manufacturing facilities at Coral Gables, Fla., is certainly capable of manufacturing the same as they currently are formulating the composition for the inventors.

In use, the crème product can be removed from the container on the tip of a finger (or squeezed out of a tube onto the finger) or applied directly to the area of the skin where hair has been removed. It is gently rubbed in and allowed to stay on the skin surface until washed off by daily washing. The crème can be applied daily, as needed or desired. The crème is intended to reduce the irritation, discomfort of rashes and ingrown hairs as a consequence of hair removal techniques. Over time, if the crème is used daily or even a few times per day, it is believed that the hair growth at the location of hair removal will become less and less and the hair's thickness, in terms of individual diameter and density per unit area, will decrease. The crème also acts as an exfolient. It has also been discovered that the present inventive crème can be an effective treatment and/or elimination and/or decrease in severity and intensity of acne and blackheads.

While the present invention is described with respect to preferred embodiments and the illustrated example, the scope of the invention is to be determined by the scope of the claims as the same are interpreted by the Courts of the US, literally and by resort to the Doctrine of Equivalents.

We claim:

1. A crème comprising a carrier and encapsulated bromelain as an active ingredient,
   wherein said bromelain is encapsulated in inert silicone,
   wherein said encapsulated bromelain is present in an amount of about 0.15% of said crème, and
   wherein said encapsulated bromelain is in the range of size of about 0.5 to 0.8 microns.

2. A crème as claimed in claim 1 wherein said inert silicone is cyclomethicone.

3. A crème as claimed in claim 1 wherein said carrier is water.

4. A crème as claimed in claim 1 wherein said composition further includes one or more of the components: stearic acid; butylenes glycol; caprylic/capric Triglycerides;
   helianthus annuus (sunflower) seed oil; glycerin; and triethanolamine.

5. A crème as claimed in claim 4 further comprising one or more of the components: Dimethicone; cetyl alcohol; polysorbate 80; gylceryl separate SE; phenoxyethanol;
   caprylyl glycol; ethylhexyglycerin; hexylene glycol; acrylates/c10-30 alkyl acrylates cross polymers; butyrospermum parkii (shea butter); melaleuca altrnifolia (Tea Tree) oil; disoldium EDTA; and Tocopheryl acetate.

6. A crème as claimed in claim 5 wherein each of said components is a component of said crème in an amount less than about 1% each.

7. A crème as claimed in claim 1 further comprising one or more of the components: Dimethicone; cetyl alcohol; polysorbate 80; gylceryl stearate SE; phenoxyethanol;
   caprylyl glycol; ethylhexyglycerin; hexylene glycol; acrylates/c10-30 alkyl acrylates cross polymers; butyrospermum parkii (shea butter); melaleuca alternifolia (Tea Tree) oil; disoldium EDTA; and Tocopheryl acetate.

8. A crème as claimed in claim 7 wherein each of said components is a component of said in an crème amount less than about 1% each.

9. A crème as claimed in claim 1 further comprising beeswax as an emulsifier.

10. A crème as claimed in claim 1 further comprising sunflower seed oil.

11. A crème as claimed in claim 1 further comprising shea butter.

12. A crème as claimed in claim 1 further comprising Tea Tree oil.

* * * * *